United States Patent [19]

Fisher et al.

[11] Patent Number: 5,491,063
[45] Date of Patent: Feb. 13, 1996

[54] METHODS FOR IN-SOLUTION QUENCHING OF FLUORESCENTLY LABELED OLIGONUCLEOTIDE PROBES

[75] Inventors: Mary E. Fisher, Oakland; Robert M. Watson, Berkeley, both of Calif.

[73] Assignee: Hoffmann-La Roche Inc., Nutley, N.J.

[21] Appl. No.: 299,682

[22] Filed: Sep. 1, 1994

[51] Int. Cl.⁶ ............................. C12Q 1/70; C12Q 1/68; C07H 19/04; C12P 19/34
[52] U.S. Cl. .......................... 435/6; 435/91.2; 435/5; 536/26.6; 536/25.32
[58] Field of Search ...................... 435/6, 91.2, 5; 536/26.6, 25.32, 24.31

[56] References Cited

U.S. PATENT DOCUMENTS 4,257,774  3/1981  Richardson .................... 23/230
5,210,015  5/1993  Gelfand et al. ................. 435/6

FOREIGN PATENT DOCUMENTS 0487218  5/1992  European Pat. Off. .

OTHER PUBLICATIONS

Cardullo et al, Detection of Nucleic Acid Hybridization by Nonradiative Fret. PNAS 85:8790–8794, 1988.
Sharp et al., 1973 "Detection of Two Restriction Endonuclease Activities in Haemophilus parainfluenzae Using Analytical Agarose–Ethidium Bromide Electrophoresis" Biochemistry 12(16):3055–3063.
Heller and Morrison, 1985, Rapid Detection and Identification of Infectious Agents, "Chemiluminescent and Fluorescent Probes for DNA Hybridization Systems" Academic Press, Inc., San Diego, CA, pp. 245–256.
Higuchi et al., Apr., 1992, "Simultaneous Amplification and Detection of Specific DNA Sequences" Bio/Technology 10:413–417.
Morrison, 1992, Nonisotopic DNA Probe Techniques, "Detection of Energy Transfer and Fluorescence Quenching", Krick Ed. Academic Press, Inc., San Diego, CA, Chapter 13.

Primary Examiner—W. Gary Jones
Assistant Examiner—Dianne Rees
Attorney, Agent, or Firm—George M. Gould; Stacey R. Sias; Douglas A. Petry

[57] ABSTRACT

The present invention is directed to methods for controlling the light emission of an oligonucleotide labeled with a light-emitting label that are useful in nucleic acid detection assays. A reaction that results in the cleavage of single-stranded oligonucleotide probes labeled with a light-emitting label is carried out in the presence of a DNA binding compound that interacts with the label to modify the light emission of the label. The methods utilize the change in light emission of the labeled probe that results from degradation of the probe. The methods are applicable in general to assays that utilize a reaction that results in cleavage of oligonucleotide probes, and, in particular, to homogeneous amplification/detection assays wherein hybridized probe is cleaved concomitant with palmer extension. A homogeneous amplification/detection assay is provided which allows the simultaneous detection of the accumulation of amplified target and the sequence-specific detection of the target sequence.

9 Claims, 3 Drawing Sheets

METHODS FOR IN-SOLUTION QUENCHING OF FLUORESCENTLY LABELED OLIGONUCLEOTIDE PROBES

BACKGROUND OF THE INVENTION

1. Field of the Invention

This invention relates generally to the field of nucleic acid chemistry. More specifically, it relates to methods of controlling the fluorescence of fluorescently labeled oligonucleotides in solution using a DNA binding compound. Additionally, it relates to methods for detecting degradation of fluorescently labeled single-stranded oligonucleotides in solution. Additionally, the invention relates to methods for detecting nucleic acid sequences by hybridization with a complementary oligonucleotide probe.

2. Description of the Related

Nucleic acid detection using oligonucleotide probes has become a standard method for specific target detection. Numerous modifications of the method have been described. Generally, a DNA sample is immobilized on a solid support and then hybridized to a labeled target-specific probe (see, for example, Falkow et al., U.S. Pat. No. 4,358,535, incorporated herein by reference).

Several nucleic acid detection methods have been described which involve selective cleavage of oligonucleotide probes following formation of probe-target hybridization duplexes. Detection of cleaved probes indicates the occurrence of hybridization and, hence, the presence of target sequences. For example, Saiki et al., 1985, *Biotechnology* 3:1008–1012, incorporated heroin by reference, describe "oligomer restriction" detection methods, in which hybridization of the target-specific probe generates a restriction site which is then cleaved by the corresponding restriction enzyme. PCT Patent Publication No. WO 89/09284, incorporated herein by reference, describes methods in which RNA probes are used to detect DNA target sequences. RNA probes hybridized to DNA target are cleaved using RNaseH, which selectively cleaves RNA in RNA-DNA hybrid duplexes. U.S. Pat. No. 5,210,015, incorporated herein by reference, describes methods which use the 5' to 3' exonuclease activity of a nucleic acid polymerase to cleave probes hybridized to target sequences and thereby release labeled oligonucleotide fragments for detection. These methods require an additional oligonucleodde hybridized upstream of the probe hybridization site to act as a primer for the polymerase-mediated extension reaction. Probe cleavage occurs concomitant with primer extension.

The invention of the polymerase chain reaction (PCR), a process for amplifying nucleic acids, enabled the detection of nucleic acids with greatly increased sensitivity and specificity. Using PCR, segments of single copy genomic DNA can be selectively amplified to an easily detectable level prior to detection. PCR methods are disclosed in U.S. Pat. No. 4,683,202, incorporated herein by reference. PCR and methods for detecting PCR products using an oligonucleotide probe capable of hybridizing with the amplified target nucleic acid are described in U.S. Pat. No. 4,683,195, and European Patent Publication No. 237,362, both incorporated herein by reference.

Similar to the methods for detecting unamplified nucleic acid described above, methods for detecting amplification product have been described which involve selective cleavage of hybridization probes following formation of probe-target hybridization duplexes. Saiki et al., 1985, *Science* 230:1350–1353, incorporated herein by reference, describe the application of "oligomer restriction" to the detection of amplified product. U.S. Pat. No. 5,210,015 also describes the analysis of PCR amplification products using the 5' to 3' exonuclease activity of a nucleic acid polymerase to cleave labeled probes hybridized to target sequences (see also Holland et al., 1991, *Proc. Natl. Acad. Sci. U.S.A.* 88:7276–7280, incorporated herein by reference). Probes that hybridize to a region of the target nucleic acid bounded by the amplification primers are incorporated into the amplification reaction mixture. Hybridized probes are cleaved by the 5' to 3' nuclease activity of the polymerase during primer extension. Detection of labeled fragments indicates the occurrence of both primer extension and probe hybridization, and, therefore, amplification of the specific target sequence.

A number of agents have been described for labeling nucleic acids, whether probe or target, for facilitating detection of target nucleic acid. Labels have been described that provide signals detectable by fluorescence, radioactivity, colorimetry, X-ray diffraction or absorption, magnetism, and enzymatic activity and include, for example, fluorophores, chromophores, radioactive isotopes (particularly $^{32}P$ and $^{125}I$), electron-dense reagents, enzymes, and ligands having specific binding partners. Labeling can be achieved by a number of means, such as chemical modification of a primer or probe to incorporate a label or the use of polymerizing agents to incorporate a modified nucleoside triphosphate into an extension product.

A variety of fluorescent DNA binding compounds are known. These include intercalating agents which bind non-covalently to the stacked bases of nucleic acids and display a change in fluorescence, either an increase or shift to a different wavelength, as a result. U.S. Pat. No. 4,582,789, incorporated herein by reference, describes several intercalating moieties including psoralens. Ethidium bromide (EtBr) is an intercalating compound that displays increased fluorescence when bound to double-stranded DNA rather than when in free solution (Sharp et al., 1973, *Biochemistry* 12:3055, incorporated herein by reference).. Although EtBr can be used to detect both single- and double-stranded nucleic acids, the affinity of EtBr for single-stranded nucleic acid is relatively low. EtBr is routinely used to non-specifically detect nucleic acids following gel electrophoresis. Following size fractionation on an appropriate gel matrix, for example, agarose or acrylamide, the gel is soaked in a dilute solution of EtBr. The DNA is then visualized by examining the gel under UV light (see Maniatis et al., 1982 eds., *Molecular Cloning: A Laboratory Manual*, New York, Cold Spring Harbor Laboratory, incorporated herein by reference).

A homogeneous assay for PCR and concurrent PCR product detection based on the increased fluorescence that ethidium bromide (EtBr) and other DNA binding labels exhibit when bound to double-stranded DNA is described in Higuchi et al., 1992, BioTechniques 10:413–417; Higuchi et al., 1993, *Bio/Techniques* 11:1026–1030; and European Patent Publication Nos. 487,218 and 512,334, each incorporated herein by reference. The methods allow direct detection of the increase of double-stranded DNA during an amplification reaction, most significantly from the increase in amplified target. However, these methods detect only the total amount of double-stranded DNA in the reaction and do not distinguish specific nucleic acid sequences; assay specificity depends on the specificity of the amplification reaction.

The use of oligonucleotide probes labeled with interacting fluorescent labels in nucleic acid hybridization assays is described in Morrison, 1992, in *Nonisotopic DNA Probe Techniques,* Kricka, ed., Academic Press, Inc., San Diego, Calif., chapter 13; and Heller and Morrison, 1985, in *Rapid Detection and Identification of Infections Agents,* Academic Press, Inc., San Diego, Calif., pages 245–256; both incorporated herein by reference. The methods rely on the change in fluorescence that occurs when suitable fluorescent labels are brought into close proximity, described in the literature as fluorescence energy transfer (FET), fluorescence resonance energy transfer, nonradiative energy transfer, long-range energy transfer, dipole-coupled energy transfer, or Förster energy transfer. A number of suitable fluorescent labels are known in the art and commercially available from, for example, Molecular Probes (Eugene, Oreg.).

Morrison, 1992, supra, described FET-based assay formats in which interacting fluorescent labels are bound to separate oligonucleotides that are either brought together or separated by probe hybridization. These assay formats, which require two probes, are described as either non-competitive or competitive, depending on whether probe-probe hybridization competes with probe-target hybridization. In an alternative assay format, one fluorescent label is bound to the hybridization probe, and the second fluorescent label is brought into close proximity by intercalating into the double-stranded hybridization duplex. No significant interaction occurs between the intercalating label and the unhybridized probe in solution. Because the intercalating label can intercalate into any double-stranded nucleic acid, this format is practical only for the detection of single stranded target nucleic acid.

In one embodiment of the nucleic acid detection methods described in U.S. Pat. No. 5,210,015, described above, a probe is used which is labeled with interacting fluorescent labels in close proximity. The labels are attached to the probe separated by one or more nucleotides such that probe degradation during amplification separates the labels, thereby producing a detectable change in fluorescence. Such multiply-labeled probes are difficult and costly to synthesize.

Conventional techniques of molecular biology and nucleic acid chemistry, which are within the skill of the art, are fully explained fully in the literature. See, for example, Sambrook et al., 1985, *Molecular Cloning—A Laboratory Manual,* Cold Spring Harbor Laboratory, Cold Spring Harbor, N.Y.; Oligonucleotide Synthesis (M. J. Gait, ed., 1984); *Nucleic Acid Hybridization* (B. D. Hames and S. J. Higgins. eds., 1984); and a series, *Methods in Enzymology* (Academic Press, Inc.), all of which are incorporated herein by reference. All patents, patent applications, and publications mentioned herein, both supra and infra, are incorporated herein by reference.

SUMMARY OF THE INVENTION

The present invention provides methods for controlling the light emission of a oligonucleotide probe labeled with a light-emitting label in solution using a DNA binding compound which can interact with the label to modify the light emission of the label.

The present invention also provides methods for detecting degradation of oligonucleotides in solution. The oligonucleotides are labeled with a light-emitting label. Oligonucleotide cleavage is carried out in the presence of a DNA binding compound that can interact with the label to modify the light emission of the label. Oligonucleotide degradation is detected by measuring the resulting change in light emission of the label.

The present invention provides conditions under which significant in-solution quenching by a DNA binding compound of a light-emitting bound to a oligonucleotide occurs. This quenching occurs without hybridization of the labeled oligonucleotide to its complementary sequence. The methods of the present invention utilize the dependence of this quenching on the length of the labeled oligonucleotide. The quenching of a light-emitting label bound to a short oligonucleotide (about 6 nucleotides or less) is detectably less than the quenching of the light-emitting label bound to a longer oligonucleotide.

Both the occurrence of in-solution quenching by a DNA binding compound of a light-emitting label bound to a single-stranded oligonucleotide and the dependence on the length of the oligonucleotide are surprising in view of the prior art. Previously-described assays (see Morrison, 1992, supra) based on the quenching by an intercalating compound of a fluorescent label bound to a probe rely on the intercalation of the quencher into a double-stranded hybridization duplex to bring the quencher and label into close proximity. The prior art teaches that in-solution quenching of label bound to unhybridized single-stranded probes is insignificant. It is well known that quenching by fluorescence energy transfer requires that the interacting labels be in close proximity, and that the two molecules in solution are not maintained in close enough proximity to cause significant quenching. Furthermore, the intercalating quenchers described in the prior art do not bind single-stranded DNA significantly, and, therefore, no appreciable quenching of a label bound to a single-stranded DNA in solution was expected. In contrast, the present invention relies on the quenching of a fluorescent label bound to a single-stranded nucleic acid by a DNA binding compound that occurs in solution.

The present invention further provides improved methods for detecting a target nucleic acid in a sample by hybridization to an oligonucleotide probe. The methods rely on the selective cleavage of probes hybridized to target nucleic acid. Detection of cleaved probes using the methods of the present invention indicates the presence of target nucleic acid.

Thus, the present invention provides a method for detecting a target nucleic acid in a sample, wherein the method comprises:

(a) providing a reaction mixture that comprises the sample, a DNA binding compound, and an oligonucleotide probe labeled with a light-emitting label, wherein said probe contains a sequence that is capable of hybridizing to the target nucleic acid, and wherein the DNA binding compound is capable of modifying the light emission of the label;

(b) measuring the light emission of the label;

(c) treating said mixture under conditions under which said oligonucleotide probe hybridizes to said target sequence and is cleaved;

(d) measuring the light emission of the label; and (e) determining if the target sequence is present by the difference in light emission between step (b) and step (d).

The selective cleavage of probes hybridized to target nucleic acid can be achieved by any of a number of known methods. Examples of suitable reactions that selectively cleave probes hybridized to a target sequence are described above in Saiki et al., 1985, supra; PCT Patent Publication No. WO 89/09284; and U.S. Pat. No. 5,210,015.

The methods of the present invention for detecting nucleic acids are particularly suited for use in conjunction with amplification processes. Thus, in one embodiment of the invention, the target sequence is amplified prior to step (c).

In a preferred embodiment, the present invention provides improvements to the homogeneous PCR amplification and PCR product detection assay described in U.S. Pat. No. 5,210,015, that use a single nucleic acid polymerase both for primer extension and for cleavage of hybridized labeled probes. The improvements provided by the present invention allow the use of a probe labeled with a single light-emitting label without requiring post-reaction manipulations to separate cleaved and uncleaved probes.

Thus, the present invention provides a method for detecting a target nucleic acid sequence in a sample using a polymerase chain reaction (PCR), wherein the method comprises:

(a) providing a PCR reaction mixture comprising said sample, a pair of oligonucleotide primers, a nucleic acid polymerase having 5' to 3' nuclease activity, a DNA binding compound, and an oligonucleotide probe capable of hybridizing to a region of the target nucleic acid bounded by the oligonucleotide primers, and wherein the probe is labeled with a light-emitting label, and wherein the DNA binding compound is capable of modifying the light emission of the label;

(b) measuring the light emission of the label;

(c) treating the PCR reaction mixture under conditions for PCR, wherein the 5' to 3' nuclease activity of the nucleic acid polymerase cleaves probes hybridized to the target sequence;

(d) measuring the light emission of the label;

(e) determining if the target sequence is present by the difference in light emission between step (b) and step (d).

In another embodiment of the homogeneous PCR amplification/detection assay, the DNA binding compound provided in the reaction mixture is characterized as providing a detectable signal when bound to double-stranded DNA, which signal is greater than the amount of said signal provided by said compound when it is unbound, and the signal of the DNA binding compound is monitored in order to measure the total increase in double-stranded DNA resulting from the amplification process. In this embodiment, the DNA binding compound functions both as a quencher of unbound probe light emission and as a signal-generating compound as used in the methods described in Higuchi et al., 1992, supra. In this embodiment of the present invention, the change in signal generated by the DNA binding compound indicates that amplification has taken place, and the change in light emission of the probe label indicates amplification of the specific target sequence. Hence, the methods provide separate measures of the success of the amplification in a homogenous assay without requiring additional reagents.

DESCRIPTION OF THE PREFERRED EMBODIMENTS

To aid in understanding the invention, several terms are defined below.

The terms "nucleic acid" and "oligonucleotide" refer to probes and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, was well as double- and single-stranded RNA.

The terms "target region", "target sequence", and "target nucleic acid sequence" refer to a region of a nucleic acid which is to be detected.

The term "probe" refers to an oligonucleotide, typically labeled, that forms a duplex structure with a sequence of a target nucleic acid due to complementary base pairing. The probe will comprise a "hybridizing region", preferably consisting of 10 to 50 nucleotides, more preferably 20 to 30 nucleotides, corresponding to a region of the target sequence. "Corresponding" means identical to or complementary to the designated nucleic acid. In the present invention, probe oligonucleotides are labeled with, i.e., bound to, a fluorescent label to enable detection.

The term "hybridization" refers the formation of a duplex structure by two single-stranded nucleic acids due to complementary base pairing. Hybridization can occur between fully complementary nucleic acid strands or between nucleic acid strands that contain minor regions of mismatch. Conditions under which only fully complementary nucleic acid strands will hybridize are referred to as "stringent hybridization conditions". Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs.

The terms "sequence-specific oligonucleotide" and "SSO" refer to oligonucleotide probes wherein the hybridizing region is exactly complementary to the sequence to be detected. The use of stringent hybridization conditions under which the probe will hybridize only to that exactly complementary target sequence allows the detection of the specific target sequence. Stringent hybridization conditions are well known in the art (see, e.g., Sambrook et al., 1985, *Molecular Cloning—A Laboratory Manual,* Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridizing conditions will allow sequence mismatches to be tolerated; the degree of mismatch tolerated can be controlled by suitable adjustment of the hybridization conditions.

The term "subsequence" refers herein to a nucleotide sequence contained within another sequence.

The term "label", as used herein, refers to any atom or molecule which can be attached to a nucleic acid, and which can be used either to provide a detectable signal or to interact with a second label to modify the detectable signal provided by the second label. Preferred labels are light-emitting compounds which generate a detectable signal by fluorescence, chemiluminescence, or bioluminescence.

The term "chromophore" refers to a non-radioactive compound that absorbs energy in the form of light. Some chromophores can be excited to emit light either by a chemical reaction, producing chemiluminescence, or by the absorption of light, producing fluorescence.

The term "fluorophore" refers to a compound which is capable of fluorescing, i.e. absorbing light at one frequency and emitting light at another, generally lower, frequency.

The term "bioluminescence" refers to a form of chemiluminescence in which the light-emitting compound is one that is found in living organisms. Examples of bioluminescent compounds include bacterial luciferase and firefly luciferase.

The term "quenching" refers to a decrease in fluorescence of a first compound caused by a second compound, regardless of the mechanism. Quenching typically requires that the compounds be in close proximity. As used herein, either the compound or the fluorescence of the compound is said to be quenched, and it is understood that both usages refer to the same phenomenon.

The term "intercalator" refers to an agent or moiety capable of non-covalent insertion between stacked base pairs in a nucleic acid double helix.

The term "homogeneous", as used herein applied to multi-step processes, refers to methods for carrying out the steps of the process, wherein the need for sample handling and manipulation between steps is minimized or eliminated. For example, a "homogeneous" amplification/detection assay refers to a coupled amplification and detection assay wherein the need for sample handling and manipulation between the amplification and detection is minimized or eliminated.

The term "reaction mixture" refers to a solution containing reagents necessary to carry out the reaction. An "amplification reaction mixture", which refers to a solution containing reagents necessary to carry out an amplification reaction, typically contains oligonucleotide primers and a DNA polymerase in a suitable buffer. Reaction mixtures for specific reactions are well-known in the literature.

The present invention provides methods for controlling the light emission of an oligonucleotide label with a light-emitting label in solution. The methods of the invention are applicable to the detection of cleavage of single-stranded oligonucleotides labeled with a single light-emitting label. Detection of the cleaved oligonucleotide is carried out in a solution containing a DNA binding compound that can interact with the label to decrease the light emission of the label. The change in the length of the labeled oligonucleotide from cleavage results in a detectable increase in the light emission of the attached label. Suitable light-emitting labels and DNA binding compounds that can interact to modify the light emission of the label are described below.

Mechanisms by which the light emission of a compound can be quenched by a second compound are described in Morrison, 1992, in *Nonisotopic DNA Probe Techniques* (Kricka ed., Academic Press, Inc. San Diego, Calif.), Chapter 13. One well known mechanism is fluorescence energy transfer (FET), also referred to in the literature as fluorescence resonance energy transfer, nonradiative energy transfer, long-range energy transfer, dipole-coupled energy transfer, and Förster energy transfer. The primary requirement for FET is that the emission spectrum of one of the compounds, the energy donor, must overlap with the absorption spectrum of the other compound, the energy acceptor. Styer and Haugland, 1967, *Proc. Natl. Acad. Sci. U.S.A.* 98:719, incorporated herein by reference, show that the energy transfer efficiency of some common emitter-quencher pairs can approach 100% when the separation distances are less than 10 angstroms. The energy transfer rate decreases proportionally to the sixth power of the distance between the energy donor and energy acceptor molecules. Consequently, small increases in the separation distance greatly diminish the energy transfer rate, resulting in an increased fluorescence of the energy donor and, if the quencher chromophore is also a fluorophore, a decreased fluorescence of the energy acceptor.

In the exemplified methods of the present invention, the emission of fluorescent label bound to the single-stranded oligonucleotide is detected. A DNA binding compound quenches the label fluorescence to a degree that depends on the length of the attached oligonucleotide. Although FET quenching is well known, both the occurrence of in-solution quenching by a DNA binding compound of a fluorescent label bound to a single-stranded oligonucleotide and the dependence of the quenching on the length of the oligonucleotide are unexpected in view of the prior art. Because of the extremely rapid decrease in interaction of fluorescent labels with increasing distance, it was believed that labels in solution do not significantly interact. The general lack of in-solution interaction is evident in the previously-described assays based on the quenching by an intercalating compound of a fluorescent label bound to a probe (see Morrison, 1992, supra). These previously-described assays rely on the intercalation of the quencher into a double-stranded hybridization duplex to bring the quencher and label into close proximity and thereby increase the quenching relative to the background unquenched state, which consists of the unhybridized labeled single-stranded probes in solution with the intercalating quencher. The intercalating quenchers described do not significantly bind single-stranded DNA, i.e., the unhybridized probe. As expected from the distance dependence of FET, the prior art does not report significant in-solution quenching of the unhybridized probe. In contrast to the teaching of the prior art, the present invention provides conditions under which significant quenching of a fluorescent label bound to a single-stranded nucleic acid by a DNA binding compound occurs in solution.

Many fluorophores and DNA-binding chromophores described in the art are suitable for use in the methods of the present invention. Suitable fluorophore and DNA-binding chromophore pairs are chosen such that the emission spectrum of the fluorophore overlaps with the absorption spectrum of the chromophore. Ideally, the fluorophore should have a high Stokes shift (a large difference between the wavelength for maximum absorption and the wavelength for maximum emission) to minimize interference by scattered excitation light.

Suitable labels which are well known in the art include, but are not limited to, fluoroscein and derivatives such as FAM, HEX, TET, and JOE; rhodamine and derivatives such as Texas Red, ROX, and TAMRA; Lucifer Yellow, and coumarin derivatives such as 7-Me$_2$N-coumarin-4-acetate, 7-OH-4-CH$_3$-coumarin-3-acetate, and 7-NH$_2$-4-CH$_3$-coumarin-3-acetate (AMCA). FAM, HEX, TET, JOE, ROX, and TAMRA are marketed by Perkin Elmer, Applied Biosystems Division (Foster City, Calif.). Texas Red and many other suitable compounds are marketed by Molecular Probes (Eugene, Oreg.). Examples of chemiluminescent and bioluminescent compounds that may be suitable for use as the energy donor include luminol (aminophthalhydrazide) and derivatives, and Luciferases.

In a preferred embodiment, the DNA binding agent is an intercalating agent. Suitable well-known intercalating agents include ethidium bromide and acridine orange.

Non-intercalating DNA binding agents are also suitable. For example, members of a class of DNA-binding compounds commonly referred to as "groove binders" are suitable. These compounds recognize and bind the minor groove of duplex DNA. Malachite Green is an example of this class of compounds that was demonstrated to function in the present methods.

In one embodiment of the invention, the DNA binding compound also provides a signal which is detectably altered upon intercalation into double-stranded DNA. Ethidium bromide, like other DNA binding labels, such as acridines, proravine, acridine orange, acriflavine, fluorcoumarin, ellipticine, daunomycin, chloroquine, distamycin D, chromomycin, homidium, mithramycin, ruthenium polypyridyls, and anthramycin, exhibits altered fluorescence emissions when bound to double-stranded DNA. Preferably, a DNA binding compound which does not inhibit an amplification reaction is used to allow monitoring of the accumulation of amplified sequences.

An oligonucleotide can be prepared by any suitable method, including, for example, cloning and isolation of appropriate sequences using restriction enzymes and direct chemical synthesis by a method such as the phosphotriester method of Narang et al., 1979, *Meth. Enzymol.* 68:90–99; the phosphodiester method of Brown et al, 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. Methods for synthesizing labeled oligonucleotides are described in Agrawal and Zamecnik, 1990, *Nucl. Acids. Res.* 18(18):5419–5423; MacMillan and Vetdine, 1990, *J. Org. Chem.* 55:5931–5933; Pieles et al., 1989, *Nucl. Acids. Res.* 17(22):8967–8978; Roger et al., 1989, *Nucl. Acids. Res.* 17(19):7643–7651; and Tesler et al., 1989, *J. Am. Chem. Soc.* 111:6966–6976, each incorporated herein by reference. A review of synthesis methods is provided in Goodchild, 1990, *Bioconjugate Chemistry* 1(3):165–187, incorporated herein by reference.

The methods of the present invention are particularly suitable for the detection of amplified nucleic acids, either DNA or RNA. Suitable amplification methods in addition to the PCR (U.S. Pat. Nos. 4,683,195; 4,683,202; and 4,965,188), include, but are not limited to, the following: Ligase Chain Reaction (LCR, Wu and Wallace, 1989, *Genomics* 4:560–569 and Barany, 1991, *Proc. Natl. Acad. Sci. U.S.A.* 88:189–193); Polymerase Ligase Chain Reaction (Barany, 1991, *PCR Methods and Applic.* 1:5–16); Gap-LCR (PCT Patent Publication No. WO 90/01069); Repair Chain Reaction (European Patent Publication No. 439,182 A2), 3SR (Kwoh et al., 1989, *Proc. Natl. Acad. Sci. U.S.A.* 86:1173–1177; Guatelli et al., 1990, *Proc. Natl. Acad. Sci. U.S.A.* 87:1874–1878; PCT Patent Publication No. WO 92/0880A), and NASBA (U.S. Pat. No. 5,130,238). All of the above references are incorporated herein by reference. This invention is not limited to any particular amplification system. As other systems are developed, those systems may benefit by practice of this invention. A recent survey of amplification systems was published in Abramson and Myers, 1993, *Current Opinion in Biotechnology* 4:41–47, incorporated herein by reference.

A preferred embodiment of the invention provides improvements to the process described in U.S. Pat. No. 5,210,015, and Holland et al., 1991, *Proc. Natl. Acad. Sci. U.S.A.* 88:7276–7280, incorporated herein by reference. The process uses the 5' to 3' exonuclease activity of a thermostable DNA polymerase to cleave annealed labeled oligonucleotide probes from hybridization duplexes and release labeled fragments for detection. Cleavage of the labeled probes of the present invention by the 5' to 3' exonuclease activity of the DNA polymerase frees the labels into the reaction mixture. The in-solution signal quenching by the DNA binding compound is significantly greater when the fluorophore is bound to the full-length uncleaved oligonucleotide probe than when bound to the shortened cleaved fragment. The resulting increase in observed fluorescence indicates probe cleavage, which necessarily indicates both the presence of target sequences and the occurrence of probe/target hybridization.

The present homogeneous PCR/detection assay is suitable for use in conjunction with the methods described in Higuchi et al, 1992, supra. In this embodiment, the fluorescence of the DNA binding compound is also measured. Thus, the fluorescence of the DNA binding agent enables detection that amplification has occurred, and the fluorescence of the cleaved hybridized probe indicates target specific amplification.

The detection methods of the present invention are applicable to a number of assays. Each assay requires a target sample in a buffer that is compatible with the assay reagents. If the target is amplified either before or simultaneously with detection of probe cleavage, the target nucleic acid must be in a buffer compatible with the enzymes used to amplify the target. The target nucleic acid can be isolated from a variety of biological materials including tissues, body fluids, feces, sputum, saliva, plant cells, bacterial cultures, and the like. Sample preparation methods suitable for each assay are described in the art.

In general, the nucleic acid in the sample will be a sequence of DNA, most usually genomic DNA. However, the present invention can also be practiced with other nucleic acids, such as messenger RNA, ribosomal RNA, viral RNA, or cloned DNA. Suitable nucleic acid samples include single or double-stranded DNA or RNA for use in the present invention. Those of skill in the art will recognize that, depending on which reaction is used to cleave the labeled oligonucleotide probes, whatever the nature of the nucleic acid, the nucleic acid can be detected merely by making appropriate and well recognized modifications to the method being used.

Sample preparation will vary depending on the source of the sample, the target to be detected, and the reaction used. Suitable sample preparation protocols are known in the art and described in the literature cited above (e.g., see Sambrook et al., supra). Simple and rapid methods of preparing samples for the PCR amplification of target sequences are described in Higuchi, 1989, in *PCR Technology* (Erlich ed., Stockton Press, New York), and in *PCR Protocols*, Chapters 18–20 (Innis et al., ed., Academic Press, 1990), both incorporated herein by reference. One of skill in the art would be able to select and empirically optimize a suitable protocol.

Fluorescence of labels in solutions is measured in a spectrofluorometer, such as a Hitachi/Perkin Elmer Model 650-40 (Perkin Elmer, Norwalk, Conn.) or a PTI LS-100 Luminescence Spectrophotometer (Photon Technology International, London, Ontario, Canada). A spectrofluorometer, depending on the features of the particular machine utilized, offers the opportunity to set the excitation and emission wavelength, as well as bandwidth. It will be obvious to one of ordinary skill in the art how to determine the wavelength and bandwidth settings for detecting the fluorescence from a particular fluorescent label. General guidance is found in, for example, *The Merck Index*, (eds. Budavari et al., 1989, Merck Co. Inc. Rahway, N.J.) and the *Molecular Probes, Inc.* (Eugene, Oreg.) *Catalog*, 1990, by Haugland, both incorporated herein by reference. Although each label has a discrete fluorescence spectrum, a broad range of detection wavelengths are suitable for practicing the invention.

Fluorescent measurements are carried out before and after the reaction that results in probe cleavage, and the change in fluorescence is calculated relative to the pre-reaction value. Equivalently, a portion of the reaction mixture is not subject to the reaction conditions. In this manner, the pre-reaction fluorescence can be measured, together with the post-reaction fluorescence, after completion of the reaction. The use of reaction vessels which are also suitable for use in measuring fluorescence allows direct measurements of both pre- and post-reaction fluorescence without opening the reaction vessel or other post-reaction manipulations.

In preferred methods in which the nucleic acid detection method is combined with PCR amplification, as described above, the amplification reaction is carded out as an automated process. Thermal cyclers are currently available from Perkin Elmer (Norwalk, Conn.) that uses a heat block capable of holding up to 48 or 96 reaction tubes. Consequently, up to 96 amplification reactions can be carded out simultaneously.

The present invention enables the automatic detection of PCR product in all samples, without the need to handle the samples, open the tubes, or interrupt the cycling reaction. Suitable optical systems, for example, are described in Higuchi et al., 1992, supra, Higuchi et al., 1993, supra, and copending and commonly assigned U.S. Ser. No. 08/113,168 and European Patent Publication No. 512,334 all incorporated herein by reference. In one such optical system, multiple fiber optic leads are used to transmit the excitation light from the source to the reaction tube and measures the emission light from each tube. Only a single fluorometer is needed to read fluorescence from the reaction tubes, as each fiber optic can be read rapidly one at a time. An alternative optical system uses a video camera to measure the fluorescence of multiple reaction vessels simultaneously. The use of transparent reaction vessel tops allows the measurement of fluorescence without opening the vessel. It will be obvious to one of skill in the art that the alternative detection apparatuses described in the '168 application also are adaptable to the present methods.

An alternative suitable detection scheme is described that uses a 96-well microliter format. This type of format is frequently desirable in clinical laboratories for large scale sample screening, for example, for genetic analysis such as screening for sickle-cell anemia or the AIDS virus in blood bank screening procedures. The present invention is suitable for this type of analysis and eliminates the need for the numerous washing and extraction procedures that are required with known "in-well" assay procedures such as ELISA type formats or other optical density-based methods.

(See Kolber et al., 1988, *J. Immun. Meth.* 108:255–264, Huschtscha et al., 1989, *In Vitro Cell and Dev. Biol.* 25(1):105–108, and Voller et al., 1979, *The Enzyme Linked Immunosorbent Assay*, Dynatech Labs, Alexandria, Va.).

The present detection methods also allow direct fluorescence measurement using an apparatus similar to ELISA plate reader, but designed to excite and measure fluorescence. For example, the CytoFluor™ 2300 machine manufactured by Millipore (Bedford, Mass.) is suitable in such a method. Alternatively, an apparatus providing a continuous determination of fluorescence is useful for monitoring the increase in PCR product during the amplification reaction.

It will be obvious to one skilled in the art that the methods of the present invention are not limited to a particular detection method, thermal cycler or signal measuring machines, or number of reaction vessels.

The methods of the present invention can be used to simultaneously detect multiple target sequences. Probes specific to each target are present in the reaction mixture. For each target nucleic acid present in the sample, the corresponding probe will hybridize and be cleaved. In order to detect the cleaved probes separately, each species of probe is labeled with a label that fluoresces at a distinct wavelength. Each species of probe is then detected separately by suitable selections of the measured wavelength.

Thus, the methods of the present invention are useful for detecting the amplification products in PCR co-amplification methods for detecting several targets in one sample without ever opening the reaction vessel once the amplification reaction is initiated. The invention is particularly useful for quantitative comparisons of two different nucleic acid targets in the same sample. Methods for quantitating nucleic acids are described in U.S. Pat. No. 5,219,727, incorporated herein by reference. The quantitation methods described are PCR-based methods using an internal standard to determine either the relative amount of a target or accurately quantitate the amount of target present prior to amplification, respectively.

The nucleotide sequence of the single-stranded oligonucleotide probes is complementary to the target sequence, in order that the probe hybridize to the target. An oligonucleotide probe may form secondary structure at low temperatures, depending on the nucleotide sequence, which results in regions of double-stranded DNA. An intercalating DNA binding compound can intercalate into the double-stranded region in close proximity to the fluorescent label, thereby increasing the efficiency of energy transfer. Although the methods of the present invention do not require the formation of double-stranded regions within the probe by secondary structure, such regions can improve the quenching of the label.

Secondary structure can be introduced into a single-stranded probe which does not form secondary structures by the addition of a terminal sequence complementary to the other terminus. The secondary structure formed involves the hybridization of the 5' and 3' ends of the probes to form a "hairpin" structure. The length of the complementary sequences at each end of the probe must be sufficient to form a stable hairpin secondary structure at the assay temperature and conditions, typically room temperature, yet not long enough so as to stabilize the hairpin secondary structure so that probe self-hybridization outcompetes probe-target hybridization, rendering the probe incapable of hybridizing to the target sequence. The exact sequence of the probe will depend on the target sequence to be detected and on the assay conditions. Preferably, complementary terminal regions about 6–9 nucleotides in length are sufficient to cause the formation of a stable hairpin structure, although more or less may be desired depending on the reaction conditions. The stability of the hairpin secondary structure of the probe and the stability of the probe-target hybridization duplex can be determined empirically.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Synthesis of Labeled Oligonucleotide Probes

Oligonucleotide probes labeled with a fluorophore at one end were synthesized on an ABI 394 DNA synthesizer (Perkin Elmer ABD, Foster City, Calif.) at a 1 micromole scale. Amidites of the fluorescent label were used during oligonucleotide synthesis to provide a 5'-labeled oligonucleotide directly. This obviated the need for any post-synthesis modification of the oligonucleotide.

The 5'-terminus of the oligonucleotide was synthesized by the addition of a phosphoramidite derivative of fluorescein (FAM, Perkin Elmer ABD, Foster City, Calif.). The phosphoramidite contains a linker separating the label from the nucleotide. After treatment of the controlled pore glass (CPG) with ammonium hydroxide at 55° C. for 4 hours to separate the labeled oligonucleotide from the CPG, the oligonucleotide was filtered off, and dried down in a stream of air, resuspended, filtered and purified by reverse phase HPLC. Fractions containing the pure 5'-labeled oligonucleotide were then evaporated to dryness.

EXAMPLE 2

The Effect of Oligonucleotide Length on the Quenching of Fluorescence

The fluorescence of labeled oligonucleotides from 2–34 nucleotides in length was measured in solutions both with and without EtBr. Additionally, measurements of the fluorescence of the free label were made for comparison.

A series of probes labeled with FAM at the 5' end was synthesized as described in Example 1. The nucleic acid sequences of the probes are provided below, oriented 5' to 3'.

present at a concentration of 1 μM. For detecting the fluorescence of the FAM label, the wavelength of the excitation light was chosen to be 495 nanometers and the fluorescence was measured at a wavelength of 518 nanometers. Readings were taken at 20° C. Measurements taken at an EtBr concentration of 4 μg/ml were repeated the following day to assess the reproducibility of the measurements.

Figure 1:
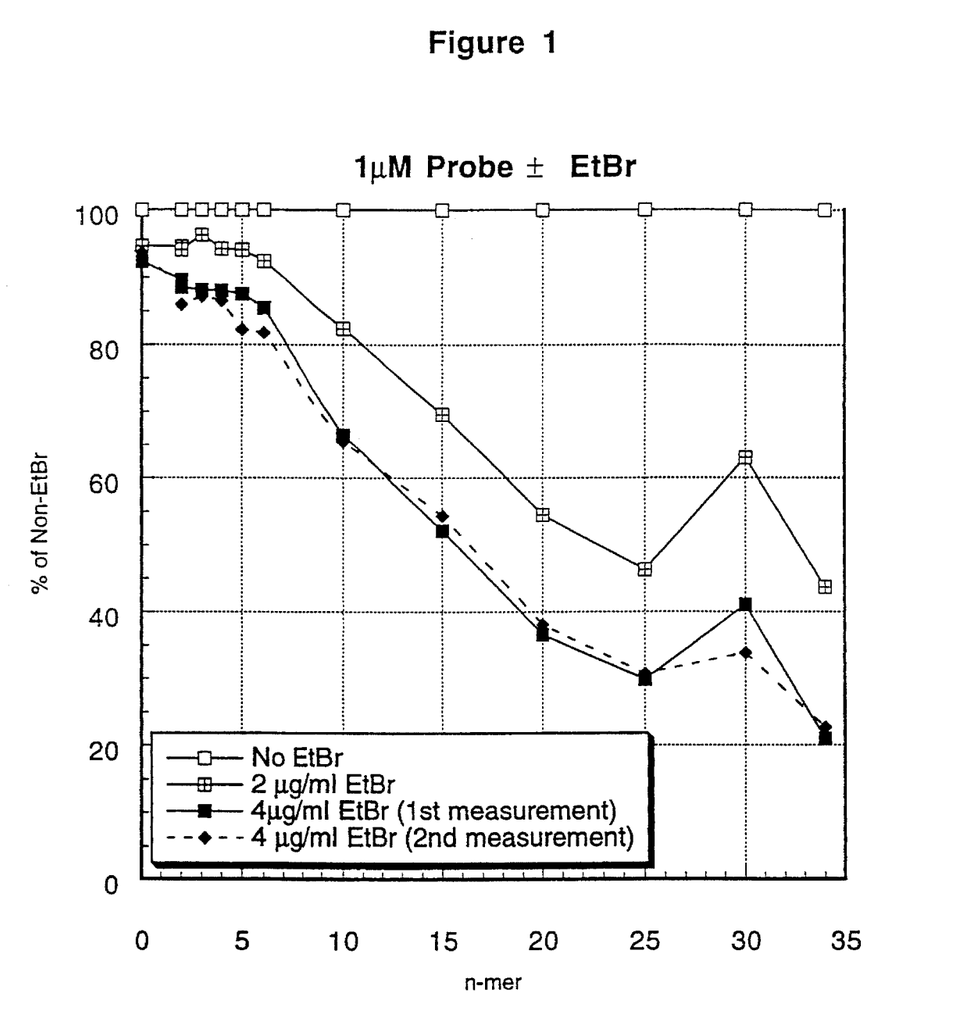
FIG. 1 relates to the dependence of in-solution fluorescent quenching on the length of the oligonucleotide to which the fluorophore is bound.

The results are presented in FIG. 1. Measurements of the probe fluorescence in the presence of EtBr are shown relative to the fluorescence without EtBr. A decrease in fluorescence of the free label in the presence of EtBr of about 6% was observed. The decrease in fluorescence of the label bound to oligonucleotides of less than 6 bases in length was not delectably different from that of the free label. Significant quenching was seen for oligonucleotides at least 10 nucleotides in length.

EXAMPLE 3

Temperature Dependence of Quenching

Experiments were carried out to determine the temperature dependence of the quenching by EtBr of fluorescein-labeled oligonucleotide probes. Fluorescence of probe solutions with and without EtBr was measured while the solutions were heated and cooled.

Solutions were prepared containing 0.5 μM of either BW118 (Seq ID No. 4) or SGW128 (Seq ID No. 6) in the buffer described in Example 2, above, both with and without 4 μg/ml EtBr. Similar solutions were prepared containing the unbound fluorescein label. Solutions not being used immediately were stored in the refrigerator in the dark until needed. To control the temperature of the solutions while measuring fluorescence, jacketed cuvettes connected to a heating water bath were used. Solution temperature was maintained by circulating water from the water bath around the solution through the jacketed cuvettes. The temperature of the circulating water was measured close to the jacketed cuvette to determine accurately the temperature of the solution being measured. Mineral oil was placed over the sample to prevent evaporation. The solution was exposed to the exciting light only while a measurement was being taken to prevent photo bleaching. Excitation and emission wavelengths were chosen as described above.

Measurements were made while the solutions were both heated and cooled. When two measurements were made at a single temperature, one during heating and one during

| Oligo | Seq ID No. | Length | Sequence |
|---|---|---|---|
| SGW70 | | 2 | GA |
| SGW71 | | 2 | CC |
| SGW74 | | 3 | GAC |
| SGW75 | | 4 | GACC |
| SGW76 | | 5 | GACCA |
| SGW77 | | 6 | GACCAG |
| BW115 | 1 | 10 | GAGACCATCA |
| BW116 | 2 | 15 | GAGACCATCAATGAG |
| BW117 | 3 | 20 | GAGACCATCAATGAGGAAGC |
| BW118 | 4 | 25 | GAGACCATCAATGAGGAAGCTGCAG |
| BW119 | 5 | 30 | GAGACCATCAATGAGGAAGCTGCAGAATGG |
| SGW128 | 6 | 34 | GACCATCAATGAGGAAGCTGCAAGAATGGGATAG |

Figure 2:
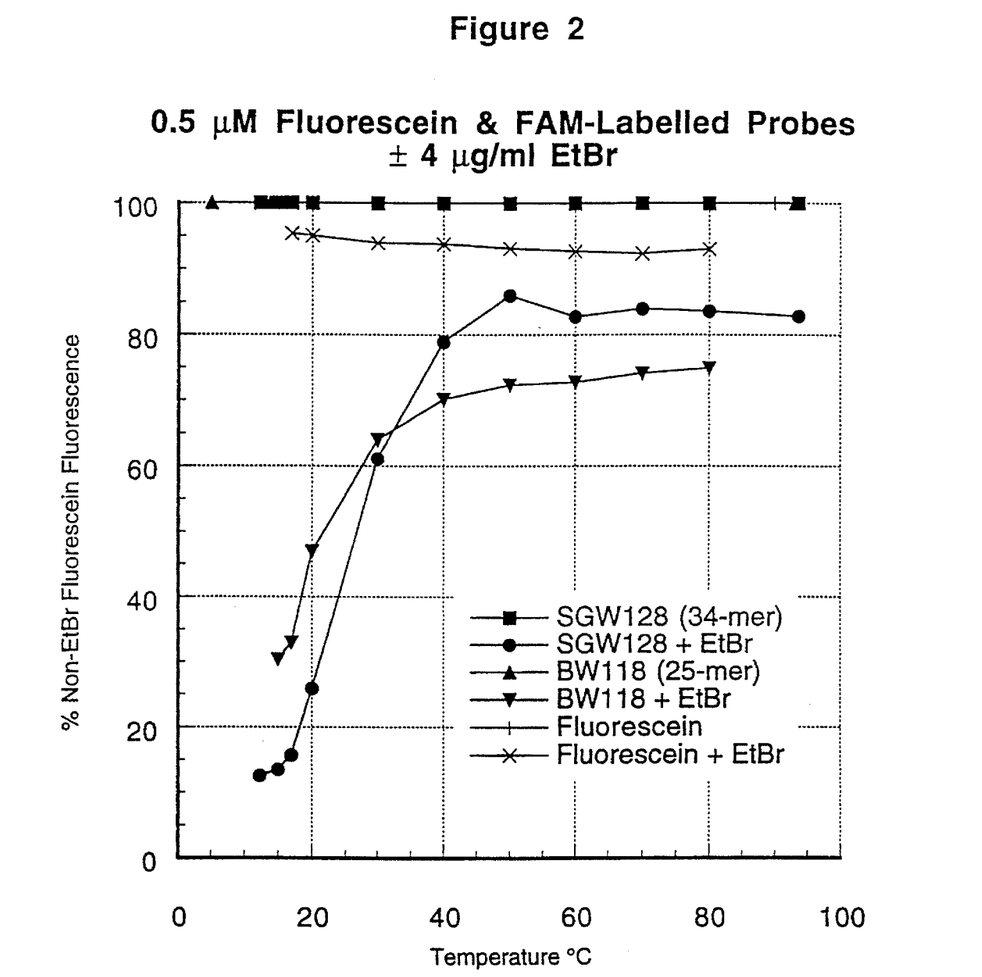
FIG. 2 relates to the dependence of in-solution fluorescent quenching on temperature.

Oligonucleotides were measured in 400 μl solutions containing a PCR reaction buffer (50 mM KCl, 10 mM Tris [pH8.3], and 3 mM MgCl$_2$), and EtBr at a concentration of 0, 2, or 4 μg/ml (0, 5, or 10 μM). The oligonucleotide was cooling, the values obtained were averaged. The data are presented in FIG. 2. Each measurement is normalized relative to the corresponding value obtained from the unquenched (without EtBr) solution.

Significant quenching of labeled oligonucleotide probes was observed at all temperatures. A significant increase in the amount of quenching was observed below 40° C., with the amount of quenching increasing with decreasing temperature throughout the observed temperature range. Although even greater quenching was observed below room temperature, it may be desirable to measure fluorescence at 20° C. for convenience.

EXAMPLE 4

PCR Probe Label Release

This example describes the use of EtBr to quench uncleaved labeled probes in a PCR reaction mixture. A PCR amplification was performed in the presence of a FAM-labeled probe which had been modified at the 3' end to prevent synthesis of an extension product. The exonuclease activity of the DNA polymerase cleaved probe hybridized to the target sequence downstream from the primer, thereby releasing small labeled oligonucleotide fragments of the probe. The increase in fluorescence of the label bound to the cleaved fragments was detected, indicating amplification of the target sequence.

Amplifications were carried out in the presence of one of the two FAM-labeled probes shown below. The nucleic acid sequences of the probes are shown in the 5' to 3' orientation. The probes were synthesized bound to FAM at the 5' end, as described above. Each probe was synthesized to have a 3'-PO$_4$ instead of a 3'-OH to block any extension by Taq polymerase.

| Probe | Seq ID No. | Sequence |
|---|---|---|
| SGW127 | 7 | CCATCAATGAGGAAGCTGCAAGAATGGGATAGAG |
| SGW128 | 8 | GACCATCAATGAGGAAGCTGCAAGAATGGGATAG |

Amplification

The amplified region was a 142 base pair product from the HIV gag region directed by primers SK431 and SK145, developed and manufactured by Hoffmann-La Roche and marketed by Perkin Elmer (Norwalk, Conn.). Amplifications were carded out from a plasmid containing a cloned fragment of the HIV gag gene.

Two replicate amplifications were carded out for each of the two probes. Amplifications were carded out in 150 µl reactions containing the following reagents:

3×10$^8$ copies of target sequence 50 mM KCl 10 mM Tris-HCl, pH 8.3

3 mM MgCl$_2$ 75 pmol each primer

50 µM each of the four deoxyribonucleoside triphosphates*

3.75 units Taq DNA polymerase (developed and manufactured by Hoffmann-La Roche and marketed by Perkin Elmer, Norwalk, Conn.)

0.5 µM probe

4 µg/ml EtBr (10 µM)

* In general, 200 µM of each deoxyribonucleotide triphosphate is preferable for the amplification of longer target regions.

For each reaction mixture subjected to PCR thermal cycling conditions, two additional reaction mixtures, one with EtBr and one without EtBr, were made and stored (no temperature cycling) for use as measurement controls. Reaction mixtures were subjected to the following amplification scheme in a GeneAmp 9600 Thermal Cycler (Perkin Elmer, Norwalk, Conn.): 35 cycles, each consisting of a denaturation step (95° C., 15 seconds) followed by an anneal/extension step (55° C. for 30 seconds), and then a final incubation to insure complete extension of products (72° C., 10 minutes). Following amplification, reactions are held at 4° C. until analyzed.

Analysis

To confirm that amplification had taken place, amplification product was analyzed by agarose gel electrophoresis. Probe degradation was analyzed as described below.

A. Analysis of Probe Degradation by Polyacrylamide Gel Electrophoresis

Following amplification, 5 µl of the amplification reaction were diluted in formamide to a probe concentration of 10 pmoles/µl. Then, 5 µl (for 50 pmoles of probe per lane) of diluted amplification reaction were loaded onto a rectangular well of a 0.4 mm thick, 7M urea, 10% polyacrylamide gel, and electrophoresed on an-ABI 373A DNA Sequencer (Perkin Elmer, Norwalk, Conn.) for 6 hours at 1500V, 20W, 20 mA (full scan sequencing run). Data were collected using the 373A DNA Sequencer Data Collection Program (Perkin Elmer, Norwalk, Conn.).

The collected data were analyzed using the 362 Gene Scanner™ Data Analysis program (v.1.2d1) (Perkin Elmer, Norwalk, Conn.). The fraction of probe cleaved was estimated by comparing the sum of the peak areas that correspond to released probe and the sum of the peak areas for the entire lane. The total amount of probe released was calculated as the estimated fraction of the total amount of probe included in the reaction mixture.

The amount of probe degradation, as measured by polyacrylamide gel electrophoresis, is shown below. The values calculated for each of the two replicate reactions are shown.

| Probe | Fraction of probe degraded | Picomoles probe released |
|---|---|---|
| 0.5 µM SGW127 | .20 | 15 |
|  | .21 | 15 |
| 0.5 µM SGW128 | .20 | 15 |
|  | .24 | 18 |

B. Analysis by Measuring Fluorescence Using a Spectrofluorometer

Fifty µl of each PCR and PCR control (uncycled reaction mixture) were diluted into 350 µl TE (10 mM Tris-HCl, 0.1 mM EDTA, pH 8.0). The fluorescence of each sample was measured at 20° C. in a Hitachi/Perkin Elmer Model 650-40 Fluorescence Spectrofluorometer (see Example 2) at an excitation wavelength of 494 nm and an emission wavelength of 522 nm. Readings were also carded out using a CytoFluor™ 2300 (described above) with a 485 nm excitation filter (20 nm band pass width) and 530 nm emission filter (25 nm band pass width).

The fraction of probe degraded can be calculated by dividing the change in fluorescence occurring during the reaction by the maximum possible change in fluorescence, i.e., the change in fluorescence that would have occurred if all the probe were degraded. The change in fluorescence occurring during the reaction is measured as the difference in fluorescence between the cycled and uncycled samples, both in the presence of EtBr, which is equivalent to measuring the reaction mixture before and after the PCR thermal cycling. No direct measurement of the maximum possible change in fluorescence was made. Instead, the maximum possible change in fluorescence was estimated as the difference between an estimate of the fluorescence of the fully degraded probe in the presence of EtBr and the fluorescence of the uncycled sample with EtBr. The estimate of the fluorescence of the fully degraded probe in the presence of EtBr was obtained as described below.

The fluorescence of the uncycled sample without EtBr, multiplied by 0.94, was used to approximate the fluorescence of a sample in the presence of EtBr in which all the probe has been degraded. Without EtBr, the fluorescence of the probe is less affected by the length of the oligonucleotide. Hence, the fluorescence of a sample containing undegraded (full-length) probes is approximately the same as a sample containing fully-degraded (short) probe. Hence, the fluorescence of the uncycled sample without EtBr is approximately the same as the fluorescence of a sample containing fully-degraded fragments without EtBr. The fluorescence of a sample containing fully-degraded fragments with EtBr is obtained after accounting for the residual quenching of the fully-degraded probe by the EtBr. As seen in FIG. 1, the residual quenching by EtBr of the fully-degraded probe fragments is approximately 6%. Therefore, multiplying the fluorescence of the uncycled sample without EtBr by a factor of 0.94 provides an estimate of the fluorescence of a sample containing fully-degraded probe in the presence of EtBr. Subtracting the fluorescence of the uncycled sample with EtBr provides the desired estimate of the maximum possible change in fluorescence.

The above approximation assumes that the difference in fluorescence between long and short probes in solution without EtBr may be ignored. In actual practice, the fluorescence of a label depends to some degree both on the length and the sequence of the attached oligonucleotide, even in the absence of EtBr. Because the dependence is unpredictable, it is preferable to measure the maximum possible change in fluorescence directly. This is carried out by making up an additional reaction mixture and adding to the reaction mixture a DNA nuclease which fully degrades the probe. The maximum change in fluorescence is calculated as the difference between the fluorescence of the reaction mixture before and after probe degradation.

The amount of probe degradation as calculated from the change in fluorescence measured using a spectrophotometer is shown below. The values calculated for each of the two replicate reactions are shown. The values are calculated using the approximation of the maximum change in fluorescence described above.

| Probe | Fraction of probe degraded | Picomoles probe released |
|---|---|---|
| 0.5 μM SGW127 | .69 | 52 |
|  | .72 | 54 |
| 0.5 μM SGW128 | .33 | 25 |
|  | .32 | 24 |

The amount of probe degradation as calculated from the change in fluorescence measured in a CytoFluor™ 2300 microwell plate reader is shown below. The values calculated for each of the two replicate reactions are shown. The values are calculated using the approximation of the maximum change in fluorescence described above.

| Probe | Fraction of probe degraded | Picomoles probe released |
|---|---|---|
| 0.5 μM SGW127 | .49 | 37 |
|  | .48 | 36 |
| 0.5 μM SGW128 | .25 | 19 |
|  | .24 | 18 |

The results demonstrate that the change in fluorescence was sufficient to enable the detection of probe degradation.

EXAMPLE 5

Augmentation of Quenching by the Secondary Structure of the Probe

The presence of secondary structure in a single-stranded oligonucleotide probe can augment the quenching by an intercalating DNA binding quencher by providing regions of double-stranded DNA into which the quencher can intercalate. This was demonstrated by comparing the quenching of probes which differ in that one probe is expected to form a hairpin structure when not hybridized to a target sequence.

Experiments were carried out essentially as described in Example 3, above, except that the temperature and fluorescence were measured continuously. Three oligonucleotides, two of which form hairpin secondary structures, were synthesized essentially as described in Example 1, above. The sequences and labeling sites are shown below.

SGW140 (Seq ID No. 9) (hairpin)
  FAM-CATAGTGGTCTGCGGAACCGGTGAGTA-CACCGACTATG
SGW146 (Seq ID No. 10) (hairpin)
  FAM-CATAGTGGTCTGCGGAACCGGTGAGTA-CACCGACTANG
ST50FLC (Seq ID No. 11)
  FAM-CATAGTGGTCTGCGGAACCGGTGAGT N represents here a modified thymidine to which TAMRA is bound.

SGW140 (Seq ID No. 9) and SGW146 (Seq ID No. 10) have self-complementary terminal regions which can hybridize to form a hairpin secondary structure. SGW146 (Seq ID No. 10) additionally contains a second quenching compound (TAMRA) bound near the 3' terminus. The formation of a hairpin structure brings the FAM and TAMRA into close proximity, thereby quenching the fluorescence. For this oligonucleotide, the combined quenching of the FAM by both TAMRA and EtBr was measured.

Measurements were carried out using a jacketed quartz cuvette in a Hitachi/Perkin Elmer Model 650-40 Fluorescence Spectrofluorometer, as described above. The excitation and emission monochromers were set to 495 and 522 nm respectively. The slit widths of the monochrometers were set at 3 and 7 nm, respectively. Measurements were carried out using 400 μl solutions containing 0.5 μM labeled oligonucleotide with and without 4 μg/ml EtBr in PCR buffer (50 mM KCl, 10 mM Tris [pH8.3], 3 mM MgCl$_2$). Solutions were stored in the refrigerator in the dark until needed.

Each sample was placed in the jacketed cuvette in the spectrofluorometer and mineral oil placed over the sample to prevent evaporation. The temperature of the solution was raised and lowered at about 1° C. per minute between about 20° and 95° C.

Figure 3:
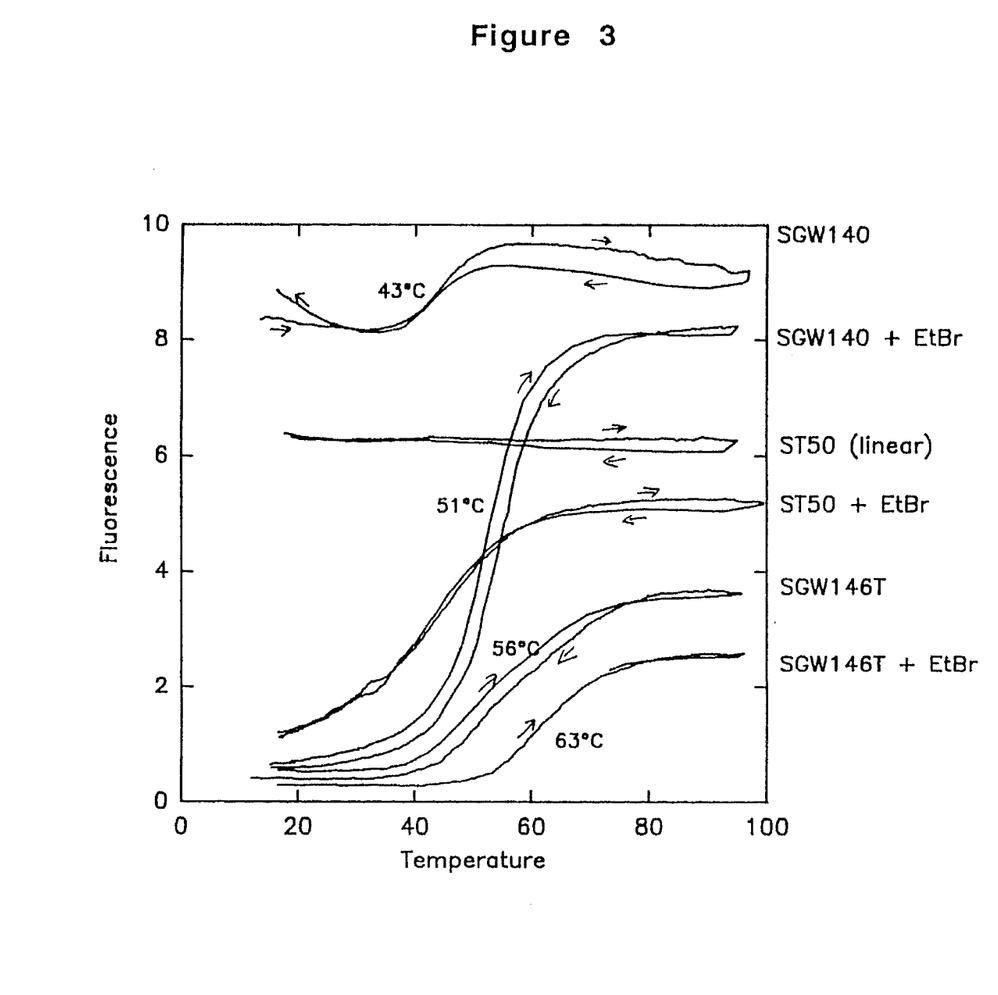
FIG. 3 relates to the dependence of in-solution fluorescent quenching on temperature and the augmentation of quenching observed resulting from the presence of a hairpin secondary structure within the labeled single-stranded oligonucleotide.

The fluorescence measurements, normalized relative to the fluorescence of the linear probe without EtBr, are presented in FIG. 3. The measurements recorded both while raising and lowering the temperature are shown. Also shown are the melting midpoints corresponding to the temperature at which the greatest rate of change of fluorescence was observed.

EtBr was observed to stabilize the double-stranded region of a hairpin probe, thereby raising the melting temperature. This can be seen in FIG. 3 comparing the shift in melting midpoints that occurred with the addition of EtBr. The presence of a hairpin secondary structure was seen to augment the fluorescent quenching by EtBr.

EXAMPLE 6

Augmentation of Quenching of a Multiply Labeled Probe

An alternative probe for use in the methods described in Example 4, above, contains a second label that acts as a quencher and is bound to the probe oligonucleotide within a few bases of the 5' terminal fluorescent label. The fluorescent label on the uncleaved probe is quenched by the second attached label by fluorescent energy transfer. Probe degradation, which occurs during primer extension, separates the label and quencher, thereby increasing the detectable signal. The use of such a probe is described in U.S. Pat. No. 5,210,015. The present methods of quenching uncleaved probes can be used in conjunction with doubly-labeled probes to further quench the uncleaved probe, thereby increasing the change in signal produced by probe degradation.

To demonstrate the additional quenching provided by combining quenchers, the fluorescence quenching by EtBr of probes labeled with FAM at the 5' end was compared to the fluorescence quenching by EtBr of probes labeled both with FAM and with Malachite Green (MG). Probes were synthesized either with only a single FAM label attached to the 5' end, or with an additional MG label attached 3 bases away from the FAM label. Both probes were synthesized with the sequence shown below.

SGW55 (Seq ID No. 12) FAM-CCANCAATGAG-GAAGCTGCAAGAATGGGATAGAG

N represents here a modified thymidine to which malachite green can be bound.

| Probe Labels | EtBr | Fluorescence | % of Max |
|---|---|---|---|
| FAM | 0 | 689 | 100% |
| FAM | 4 μg/ml | 106 | 15% |
| FAM + MG | 0 | 165 | 24% |
| FAM + MG | 4 μg/ml | 46.1 | 7% |

Quenching either by EtBr in the PCR reagent mixture or by the additional label is sufficient to produce a detectable change in the signal. The combination of quenching methods provides a significant increase in quenching efficiency, allowing more sensitive discrimination of the cleaved and uncleaved probe. The use of a multiply-labeled probe, as described herein, in the methods described in Example 4, above, would further enhance the ability to distinguish between the cleaved and uncleaved probes.

EXAMPLE 7

Quenching by Other DNA Binding Compounds

The selection of another suitable DNA binding compound for the in-solution quenching of fluorescently-labeled probes was demonstrated using the following series of fluorescent DNA binding compounds: PO-PRO-1, BO-PRO-1, YO-PRO-1, and TO-PRO-1. These compounds are related monomeric cyanine nucleic acid stains which are commercially available from Molecular Probes (Eugene, Oreg.). The excitation and emission maxima, measured in nanometers, for each of the compounds is provided below. The excitation and emission maxima of the fluorescein label is shown for comparison.

| Compound | Excitation and Emission Maxima | |
|---|---|---|
|  | Excitation | Emission |
| PO-PRO-1 | 435 | 455 |
| BO-PRO-1 | 462 | 481 |
| YO-PRO-1 | 491 | 509 |
| TO-PRO-1 | 515 | 531 |
| Fluorescein | 494 | 516 |

Maximal interaction between a fluorescein label and a DNA binding compound is expected to occur when the emission maxima of the fluorescein (516 nm) most closely matches the excitation maxima of the DNA binding compound. Hence, TO-PRO- 1 was expected to exhibit the greatest quenching of a fluorescein label, and PO-PRO- 1 was expected to exhibit the least.

Oligonucleotides of lengths 33 and 2 were synthesized as described above. The sequences of the two oligonucleotides are shown below, oriented 5' to 3'. The oligonucleotide of length 2 corresponds to a degraded form of the full-length oligonucleotide.

| Oligo | SEQ ID NO: | Sequence |
|---|---|---|
| ST535FS | 13 | FAM-AGAAGGTGAGATGACCAGAGGACTGAGTCCAAT |
| ST4F |  | FAM-AG |

Measurements of the fluorescence were carried out essentially as described in Example 2, above. The results are presented below.

The fluorescence of the labeled oligonucleotides in solution with and without one of the above DNA binding compounds was measured essentially as in Example 2, above, using a PTI LS-100 Luminescence Spectrophotometer (Photon Technology International, London, Ontario, Canada). Measurements were carried out in 400 µl solutions containing 0.5 µM oligonucleotide, 1×PCR buffer (50 mM KCl, 10 mM Tris [pH 8.3], and 3 mM MgCl$_2$) and with or without 5 µM of one of the DNA binding compounds. The amount of quenching, expressed as a percent of the unquenched signal, for each oligonucleotide and DNA binding compound, is presented below.

|  | Quenching | |
| --- | --- | --- |
| Quencher | ST535FS | ST4F |
| PO-PRO-1 | 6.0 | 1.1 |
| BO-PRO-1 | 20.4 | 2.1 |
| YO-PRO-1 | 20.7 | 19.0 |
| TO-PRO-1 | 95.9 | 29.6 |

The present methods rely on differential quenching of long and short oligonucleotides. As expected from a comparison of emission and excitation maxima, the fluorescence quenching of fluorescein by TO-PRO-1 was observed to be the greatest, and the fluorescence quenching of fluorescein by PO-PRO-1 was observed to be the least. TO-PRO-1 also exhibited greatly reduced quenching of the labeled 2-nucleotide fragment. The over 3-fold difference in quenching (from −96% to −30%) is sufficient to allow the sensitive detection of oligonucleotide cleavage in a reaction using the present methods.

The results suggest that the predominant mechanism of quenching may be FET and that other suitable label/quencher pairs can be predictably selected by a comparison of label emission and quencher excitation maxima. Following selection, optimal quencher concentration which maximizes the difference between the quenching of long and short labeled oligonucleotides can be determined by routine screening, as described below.

The optimal concentration of TO-PRO-1 for use in the preset methods was determined as follows. The fluorescence quenching of each of the above probes was measured in solutions containing TO-PRO-1 at concentrations of from 0 to 10 µM. The measurements were carried out essentially as described above. The results are presented below.

|  | Residual Fluorescence | |
| --- | --- | --- |
| TO-PRO-1 (µM) | ST4F | ST535FS |
| 0.0 | 1.0 | 1.0 |
| 0.1 | 1.0 | 1.0 |
| 0.5 | 0.97 | 0.87 |
| 0.75 | 0.95 | 0.74 |
| 1.0 | 0.91 | 0.65 |
| 5.5 | 0.81 | 0.21 |
| 5.0 | 0.70 | 0.06 |
| 10.0 | 0.45 | 0.01 |

The data shown were not corrected for the absorption by TO-PRO-1 at the excitation and emission wavelengths of fluorescein. The significant quenching of the short oligonucleotide at high concentrations of TO-PRO-1 is attributable to the optical density of TO-PRO-1 and not due to quenching of the fluorescein. A TO-PRO-1 concentration of 5.0 µM would provide the greatest difference in quenching between full-length and degraded probes.

We claim:

1. A method for controlling the light emission of a single-stranded oligonucleotide covalently labeled with a light-emitting label in solution comprising incorporating into said solution a DNA binding compound, wherein said DNA binding compound can interact with said label to modify the light emission of said label.

2. The method of claim 1, wherein said DNA binding compound is a DNA intercalator.

3. The method of claim 2, wherein said label is a fluorescein derivative and said DNA binding compound is ethidium bromide.

4. A method for detecting cleavage of a single-stranded oligonucleotide covalently labeled with a light-emitting label, wherein said cleavage is catalyzed by a reaction, and wherein said method comprises:

(a) providing a reaction mixture suitable for carrying out said reaction, wherein said reaction mixture comprises said oligonucleotide and a DNA binding compound, wherein said DNA binding compound is capable of interacting with said label to modify the light emission of said label;

(b) measuring the light emission of said oligonucleotide in said reaction mixture;

(c) carrying out said reaction under conditions which result in the cleavage of said oligonucleotide, (d) measuring the light emission of said oligonucleotide in said reaction mixture;

(e) detecting cleavage of said oligonucleotide by the difference between the light emission measured in step (b) and step (d).

5. The method of claim 4, wherein said DNA binding compound is a DNA intercalator.

6. The method of claim 5, wherein said label is a fluorescein derivative and said DNA binding compound is ethidium bromide.

7. A method for detecting a target nucleic acid sequence in a sample using a polymerase chain reaction (PCR), wherein the process comprises:

(a) providing a PCR reaction mixture comprising said sample, a pair of oligonucleotide primers, a nucleic acid polymerase having 5' to 3' nuclease activity, a DNA binding compound, and an oligonucleotide probe capable of hybridizing to a region of said target nucleic acid, wherein said oligonucleotide probe hybridizes within said target nucleic acid sequence bounded by said oligonucleotide primers, and wherein said oligonucleotide probe is covalently labeled with a light-emitting label, and wherein said DNA binding compound is capable of modifying the light emission of said label;

(b) measuring the light emission of said label in said reaction mixture;

(c) treating the PCR reaction mixture under conditions for PCR, wherein the 5' to 3' nuclease activity of the nucleic acid polymerase cleaves probes hybridized to the target sequence;

(d) measuring the light emission of said label in said reaction mixture;

(e) determining if said target sequence is present by the difference between the light emission measured in step (b) and the light emission measured in step (d).

8. The method of claim 7, wherein said DNA binding compound is a DNA intercalator.

9. The method of claim 8, wherein said label is a fluorescein derivative and said DNA binding compound is ethidium bromide.

* * * * *

UNITED STATES PATENT AND TRADEMARK OFFICE
CERTIFICATE OF CORRECTION

PATENT NO. : 5,491,063
DATED : February 13, 1996
INVENTOR(S) : Mary E. Fisher and Robert M. Watson Page 1 of 2

It is certified that error appears in the above-indentified patent and that said Letters Patent is hereby corrected as shown below:

On The Title page, in the Abstract, item No.[57], line 14, please delete "palmer" and insert therefor --primer--.

In column 1, at line 32, please delete "heroin" and insert therefor --herein--.

In column 1, at line 46, please delete "oligonucleodde" and insert therefor --oligonucleotide--.

In column 2, at line 40, please delete ".." and insert therefor --.--.

In column 11, at line 32, please delete "carded" and insert therefor --carried--.

In column 11, at line 36, please delete "carded" and insert therefor --carried--.

In column 15, at line 44, please delete "carded" and insert therefor --carried--.

In column 15, at line 46, please delete "carded" and insert therefor --carried--.

In column 15, at line 47, please delete "carded" and insert therefor --carried--.

In column 16, at line 26, please delete "an-ABI" and insert therefor --an ABI--.

UNITED STATES PATENT AND TRADEMARK OFFICE
CERTIFICATE OF CORRECTION

PATENT NO. : 5,491,063
DATED : February 13, 1996
INVENTOR(S) : Mary E. Fisher and Robert M. Watson It is certified that error appears in the above-indentified patent and that said Letters Patent is hereby corrected as shown below:

In column 16, at line 66, please delete "carded" and insert therefor --carried--.

Signed and Sealed this

Twenty-ninth Day of October 1996

Attest:

BRUCE LEHMAN

*Attesting Officer*       *Commissioner of Patents and Trademarks*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

GAGACCATCA     10

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

GAGACCATCA ATGAG     15

( 2 ) INFORMATION FOR SEQ ID NO:3:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

GAGACCATCA ATGAGGAAGC                                                         20

(2) INFORMATION FOR SEQ ID NO:4:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:4:

GAGACCATCA ATGAGGAAGC TGCAG                                                   25

(2) INFORMATION FOR SEQ ID NO:5:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

GAGACCATCA ATGAGGAAGC TGCAGAATGG                                              30

(2) INFORMATION FOR SEQ ID NO:6:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:6:

GACCATCAAT GAGGAAGCTG CAAGAATGGG ATAG                                         34

(2) INFORMATION FOR SEQ ID NO:7:

(i) SEQUENCE CHARACTERISTICS:
    (A) LENGTH: 34 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:7:

CCATCAATGA GGAAGCTGCA AGAATGGGAT AGAG                                         34

(2) INFORMATION FOR SEQ ID NO:8:

(i) SEQUENCE CHARACTERISTICS:
    (A) LENGTH: 34 base pairs
    (B) TYPE: nucleic acid
    (C) STRANDEDNESS: single (D) TOPOLOGY: linear (ii) MOLECULE TYPE: DNA (genomic)

(xi) SEQUENCE DESCRIPTION: SEQ ID NO:8:

GACCATCAAT GAGGAAGCTG CAAGAATGGG ATAG 34

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:9:

CATAGTGGTC TGCGGAACCG GTGAGTACAC CGACTATG 38

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:10:

CATAGTGGTC TGCGGAACCG GTGAGTACAC CGACTANG 38

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:11:

CATAGTGGTC TGCGGAACCG GTGAGT 26

(2) INFORMATION FOR SEQ ID NO:12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:12:

CCANCAATGA GGAAGCTGCA AGAATGGGAT AGAG 34

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:13:

AGAAGGTGAG ATGACCAGAG GACTGAGTCC AAT          33